US00PP15313P2

(12) United States Plant Patent
Kester

(10) Patent No.: US PP15,313 P2
(45) Date of Patent: Nov. 16, 2004

(54) *CHRYSANTHEMUM* PLANT NAMED 'PANUCO'

(50) Latin Name: *Chrysanthemum×morifolium*
Varietal Denomination: Panuco

(75) Inventor: Jozef A. J. Kester, De Lier (NL)

(73) Assignee: Fides Goldstock Breeding, Inc., DeLier (NL)

( * ) Notice: Subject to any disclaimer, the term of this patent is extended or adjusted under 35 U.S.C. 154(b) by 0 days.

(21) Appl. No.: 10/770,222

(22) Filed: Feb. 2, 2004

(51) Int. Cl.[7] ..... A01H 5/00

(52) U.S. Cl. ..... Plt./298

(58) Field of Search ..... Plt./298

*Primary Examiner*—Anne Marie Grunberg
(74) *Attorney, Agent, or Firm*—C. A. Whealy

(57) ABSTRACT

A new and distinct cultivar of cut flower *Chrysanthemum* plant named 'Panuco', characterized by its upright growth habit; freely flowering habit; daisy-type inflorescences; attractive dark red purple-colored ray florets; response time about 49 days when grown at 18° C.; dark green-colored foliage; strong flowering stems and peduncles; and good postproduction longevity with inflorescences and foliage maintaining good substance and color for about two weeks in an interior environment.

1 Drawing Sheet

Botanical classification/cultivar designation: *Chrysanthemum×morifolium* cultivar Panuco.

BACKGROUND OF THE INVENTION

The present invention relates to a new and distinct cultivar of cut flower *Chrysanthemum* plant, botanically known as *Chrysanthemum×morifolium* and hereinafter referred to by the name 'Panuco'.

The new *Chrysanthemum* is a product of a planned breeding program conducted by the Inventor in De Lier, The Netherlands. The objective of the breeding program is to create new high-yielding cut flower *Chrysanthemum* cultivars with attractive ray and disc coloration, good inflorescence form and substance and good post-production longevity.

The new *Chrysanthemum* originated from a cross-pollination made by the Inventor in January, 1999, in De Lier, The Netherlands, of a proprietary *Chrysanthemum×morifolium* selection identified as code number 2B 4, not patented, as the female, or seed, parent with a proprietary *Chrysanthemum×morifolium* selection identified as 12B 6, not patented, as the male, or pollen, parent.

The cultivar Panuco was discovered and selected by the Inventor as a flowering plant within the progeny of the stated cross-pollination in a controlled environment in De Lier, The Netherlands in August, 1999. The selection of this plant was based on its desirable inflorescence coloration and good form and substance.

Asexual reproduction of the new *Chrysanthemum* by vegetative tip cuttings in a controlled environment in De Lier, The Netherlands since January, 2000, has shown that the unique features of this new *Chrysanthemum* are stable and reproduced Panuco to type in successive generations.

SUMMARY OF THE INVENTION

Plants of the cultivar Panuco have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Panuco'. These characteristics in combination distinguish 'Panuco' as a new and distinct cultivar:

1. Upright cut *Chrysanthemum* that is usually grown as a natural spray.
2. Freely flowering habit, about 18 inflorescences per flowering stem.
3. Daisy-type inflorescences.
4. Attractive dark red purple-colored ray florets.
5. Response time about 49 days when grown at 18° C.
6. Dark green-colored foliage.
7. Strong flowering stems and peduncles.
8. Good postproduction longevity with inflorescences and foliage maintaining good substance and color for about two weeks in an interior environment.

Plants of the new *Chrysanthemum* can be compared to plants of the female parent selection. In side-by-side comparisons conducted in De Lier, The Netherlands, plants of the new *Chrysanthemum* differed from plants of the female parent selection in the following characteristics:

1. Flowering stems of plants of the new *Chrysanthemum* were longer than flowering stems of plants of the female parent selection.
2. Plants of the new *Chrysanthemum* flowered two days earlier than plants of the female parent selection.
3. Plants of the new *Chrysanthemum* had longer postproduction longevity than plants of the female parent selection.
4. Ray florets of plants of the new *Chrysanthemum* were dark red purple in color whereas ray florets of plants of the female parent selection were red in color.

Plants of the new *Chrysanthemum* can be compared to plants of the male parent selection. In side-by-side comparisons conducted in De Lier, The Netherlands, plants of the new *Chrysanthemum* differed from plants of the male parent selection in the following characteristics:

1. Flowering stems of plants of the new *Chrysanthemum* were shorter than flowering stems of plants of the male parent selection.
2. Plants of the new *Chrysanthemum* had smaller inflorescences than plants of the male parent selection.
3. Plants of the new *Chrysanthemum* flowered about two days later than plants of the male parent selection.

Plants of the new *Chrysanthemum* can also be compared to plants of the *Chrysanthemum×morifolium* cultivar Splended Reagan, disclosed in U.S. Plant Pat. No. 10,205. In side-by-side comparisons conducted in De Lier, The Netherlands, plants of the new *Chrysanthemum* differed from plants of the cultivar Splendid Reagan in the following characteristics:

1. Plants of the new *Chrysanthemum* had smaller inflorescences than plants of the cultivar Splended Reagan.
2. Plants of the new *Chrysanthemum* flowered about five days earlier than plants of the cultivar Splended Reagan.
3. Ray florets of plants of the new *Chrysanthemum* were darker in color than ray florets of plants of the cultivar Splendid Reagan.

Plants of the new *Chrysanthemum* can also be compared to plants of the *Chrysanthemum×morifolium* cultivar Lineker, not patented. In side-by-side comparisons conducted in De Lier, The Netherlands, plants of the new *Chrysanthemum* differed from plants of the cultivar Lineker in the following characteristics:

1. Flowering stems of plants of the new *Chrysanthemum* were shorter and thinner than flowering stems of plants of the cultivar Lineker.
2. Plants of the new *Chrysanthemum* flowered about two days earlier than plants of the cultivar Lineker.
3. Plants of the new *Chrysanthemum* had smaller inflorescences than plants of the cultivar Lineker.
4. Ray florets of plants of the new *Chrysanthemum* were darker in color than ray florets of plants of the cultivar Lineker.

BRIEF DESCRIPTION OF THE PHOTOGRAPH

The accompanying colored photograph illustrates the overall appearance of the new *Chrysanthemum*, showing the colors as reasonably possible to obtain in colored reproductions of this type. Colors in the photograph may differ slightly from the color values cited in the detailed botanical description which accurately describe the colors of the new *Chrysanthemum*.

The photograph comprises a side perspective view of a typical flowering stem of 'Panuco' grown as a natural spray.

DETAILED BOTANICAL DESCRIPTION

The aforementioned photograph and following observations and measurements describe plants grown in De Lier, The Netherlands, under conditions which approximate commercial practice in a glass-covered greenhouse in June. Cuttings were planted in ground beds and received two weeks of long day/short nights followed by short day/long nights until flowering. Plants were grown as single-stem natural spray cut *Chrysanthemums*. During the production of the flowering plants, day and night temperatures averaged 18.5° C. The photograph and botanical description were taken about ten weeks after planting. In the following description, color references are made to The Royal Horticultural Society Colour Chart, 2001 Edition, except where general terms of ordinary dictionary significance are used.

Botanical classification: *Chrysanthemum×morifolium* cultivar Panuco.

Commercial classification: Daisy-type cut flower *Chrysanthemum.*

Parentage:

*Female or seed parent.*—Proprietary *Chrysanthemum× morifolium* selection identified as code number 2B 4, not patented.

*Male or pollen parent.*—Proprietary *Chrysanthemum× morifolium* selection identified as code number 12B 6, not patented.

Propagation:

*Type.*—Vegetative tip cuttings.

*Time to initiate roots.*—Summer: About five days at temperatures of 20° C. Winter: About six days at temperatures of 20° C.

*Time to produce a rooted young plant.*—Summer: About 11 days at temperatures of 20° C. Winter: About 15 days at temperatures of 20° C.

*Root description.*—Fine, fibrous and white in color.

*Rooting habit.*—Freely branching.

Plant description:

*Appearance/growth habit.*—Herbaceous daisy-type cut flower that is typically grown as a natural spray. Narrow columnar; moderately vigorous to vigorous.

*Flowering stem description.*—Aspect: Erect. Length: About 76 cm. Diameter (natural spray diameter): About 21 cm. Diameter: About 6 mm. Internode length: About 2.3 cm. Texture: Pubescent; longitudinally ridged. Strength: Strong. Color: Between 138A and 143A.

*Foliage description.*—Arrangement: Alternate; single. Length: About 9.1 cm. Width: About 5.3 cm. Apex: Broadly acute. Base: Attenuate. Margin: Palmately lobed; sinuses convergent to parallel. Texture, upper and lower surfaces: Sparsely pubescent; slightly rough. Color: Developing foliage, upper surface: Between 137A and 143A. Developing foliage, lower surface: 138A to 138B. Fully expanded foliage, upper surface: 137A. Fully expanded foliage, lower surface: 137C. Venation, upper surface: 138B. Venation, lower surface: 138C to 138D. Petiole: Length: About 2.2 cm. Diameter: About 3.5 mm. Color, upper and lower surfaces: 138B.

Flowering description:

*Appearance.*—Daisy-type inflorescence form with obovate-shaped ray florets. Inflorescences borne on terminals, arising from leaf axils. Disc and ray florets develop acropetally on a capitulum.

*Flowering response.*—Under natural conditions, plant flower mid-October to early November in The Netherlands. At other times of the year, inflorescence initiation and development can be induced under short day/long night conditions (at least 13.5 hours of darkness). Plants exposed to two weeks of long day/short night conditions after planting followed by photoinductive short day/long night conditions flower about 49 days later when grown as a natural spray.

*Postproduction longevity.*—In an interior environment, inflorescences and foliage will maintain good color and substance for about two weeks in an interior environment.

*Quantity of inflorescences*.—Freely flowering habit, about 18 inflorescences per flowering stem.

*Inflorescence size*.—Diameter: About 4.4 cm. Depth (height): About 1.8 cm. Disc diameter: About 1.5 cm. Receptacle diameter: About 1.5 cm. Receptacle height: About 4 mm.

*Inflorescence buds*.—Shape: Oblate. Height: About 6 mm. Diameter: About 7 mm. Color: Between 137A and 143A.

*Ray florets*.—Shape: Obovate. Length: About 1.7 cm. Width: About 8 mm. Apex: Obtuse to retuse. Base: Attenuate. Texture: Smooth, glabrous; longitudinally ridged. Aspect: Initially upright; when fully expanded horizontal to about 15° from horizontal. Number of ray florets per inflorescence: About 25 arranged in two rows. Color: When opening, upper surface: 59A. When opening, lower surface: 64A to 64C. Fully opened, upper surface: Slightly darker than 59A to 61A. Fully opened, lower surface: 64A to 64C.

*Disc florets*.—Arrangement: Massed at center of receptacle. Shape: Tubular, elongated. Apex: Five-pointed. Length: About 5 mm. Width: Apex: About 1 mm. Base: About 0.8 mm. Number of disc florets per inflorescence: About 200. Color: Immature: 151C to 151D. Mature: Apex: 145B to 145C. Mid-section: 151C to 151D. Base: 12A to 12B.

*Phyllaries*.—Quantity per inflorescence: About 15. Length: About 7 mm. Width: About 3 mm. Shape: Ovate. Apex: Obtuse. Base: Broadly cuneate. Margin: Entire. Texture, upper and lower surfaces: Densely pubescent. Color, upper surface: 143A. Color, lower surface: Between 137A and 143A.

*Peduncles*.—Length: First peduncle: About 6.5 cm. Fourth peduncle: About 6.5 cm. Seventh peduncle: About 9.2 cm. Diameter: About 2 mm. Angle: About 25° from vertical. Strength: Strong. Texture: Densely pubescent. Color: 143A.

*Reproductive organs*.—Androecium: Present on disc florets only. Anther color: 12A. Pollen amount: Moderate. Pollen color: 12A to 13A. Gynoecium: Present on both ray florets. Stigma color: 12A. Ovary color: 151C to 151D.

*Seed/fruit*.—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of 10° C. and high temperatures of 35° C.

It is claimed:

1. A new and distinct cultivar of cut flower *Chrysanthemum* plant named 'Panuco', as illustrated and described.

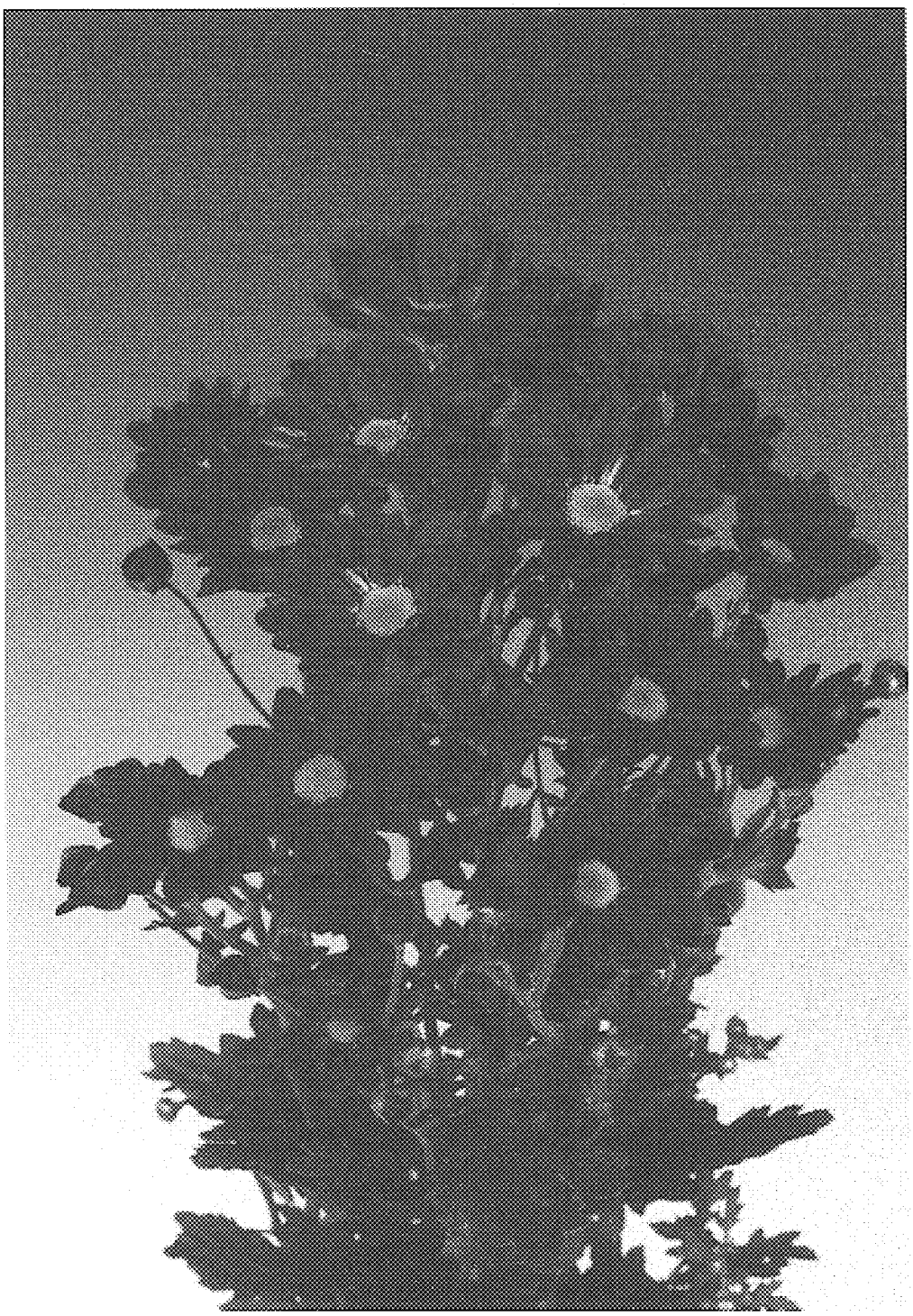

* * * * *